(12) United States Patent
Chen et al.

(10) Patent No.: US 10,794,887 B2
(45) Date of Patent: Oct. 6, 2020

(54) INTELLIGENT DEVICE FOR INTEGRATED SAMPLING OF LAYERED WATER AND SEDIMENT CORE OF DEEP RESERVOIR

(71) Applicant: Nanjing Hydraulic Research Institute, Nanjing (CN)

(72) Inventors: Qiuwen Chen, Nanjing (CN); Juhua Yu, Nanjing (CN); Jianyun Zhang, Nanjing (CN); Wenyong Yu, Nanjing (CN); Wenqing Shi, Nanjing (CN); Yuqing Lin, Nanjing (CN); Liuming Hu, Nanjing (CN); Zhiyuan Wang, Nanjing (CN)

(73) Assignee: Nanjing Hydraulic Research Institute, Nanjing (CN)

( * ) Notice: Subject to any disclaimer, the term of this patent is extended or adjusted under 35 U.S.C. 154(b) by 51 days.

(21) Appl. No.: 16/297,454

(22) Filed: Mar. 8, 2019

(65) Prior Publication Data
US 2019/0204287 A1  Jul. 4, 2019

(51) Int. Cl.
*G01N 1/10* (2006.01)
*G01N 1/08* (2006.01)
(Continued)

(52) U.S. Cl.
CPC ............. *G01N 33/18* (2013.01); *G01N 1/08* (2013.01); *G01N 35/04* (2013.01); *G01N 1/16* (2013.01);
(Continued)

(58) Field of Classification Search
CPC ............ G01N 1/14; G01N 1/10; G01N 33/18; G01N 2001/1427; G01N 1/08;
(Continued)

(56) References Cited

U.S. PATENT DOCUMENTS

| | | | | |
|---|---|---|---|---|
| 4,403,519 A | * | 9/1983 | Welker | ................ B01F 11/0082 366/332 |
| 10,094,091 B1 | * | 10/2018 | Tesvich | .................... E02B 3/023 |
| 2020/0011768 A1 | * | 1/2020 | Dong | ........................ G01N 1/14 |

FOREIGN PATENT DOCUMENTS

| | | |
|---|---|---|
| CN | 201559799 U | 8/2010 |
| CN | 202853932 U | 4/2013 |

(Continued)

*Primary Examiner* — Brandi N Hopkins
(74) *Attorney, Agent, or Firm* — CBM Patent Consulting, LLC

(57) ABSTRACT

An ultra-deep reservoir stratified water sample and sediment core integrated artificial intelligence sampling device, comprising a sampling device main chamber, an attitude balance sensor, a propeller, a balance base, and a sampler body, wherein the attitude balance sensor and the sampler body are disposed inside the sampling device main chamber; the propeller is disposed outside the sampling device main chamber; and the balance base is located at a bottom end of the sampling device main chamber. The sampling device of the present invention is an intelligent sampling device integrating high-definition underwater topography observation, undisturbed sediment core collection, vertical stratified accurate sampling of water bodies, and real-time in-situ monitoring of key physical and chemical parameters, and can be flexibly applied to deep and shallow water environments under complicated conditions.

6 Claims, 2 Drawing Sheets

(51) Int. Cl.
    *G01N 33/18*     (2006.01)
    *G01N 35/04*     (2006.01)
    *G01N 1/16*     (2006.01)

(52) U.S. Cl.
    CPC ........... *G01N 2035/0403* (2013.01); *G01N 2035/0406* (2013.01); *G01N 2035/0412* (2013.01); *G01N 2035/0441* (2013.01)

(58) Field of Classification Search
    CPC ........ G01N 35/04; G01N 2035/0406; G01N 2035/0412; G01N 1/16; G01N 2035/0441; G01N 2035/0403; G01D 21/02
    See application file for complete search history.

(56) References Cited

FOREIGN PATENT DOCUMENTS

| | | |
|---|---|---|
| CN | 204302048 U | 4/2015 |
| CN | 105675835 A | 6/2016 |
| CN | 205785906 U | 12/2016 |

\* cited by examiner

INTELLIGENT DEVICE FOR INTEGRATED SAMPLING OF LAYERED WATER AND SEDIMENT CORE OF DEEP RESERVOIR

TECHNICAL FIELD

The present invention belongs to the technical field of collection of key environmental samples of sediments and overlying water under ultra-deep reservoir complicated conditions and real-time field monitoring of physical and chemical water parameters, and more particularly relates to a deep reservoir water sample and sediment integrated artificial intelligence collection device.

BACKGROUND ART

In the fields of environmental science, ecology, geosciences and marine limnology, sediments are widely used as important information carriers for studying human-natural interactions at different time scales due to complete and faithful records of various types of information of environmental changes in aquatic ecosystems. Therefore, it is essential to invent an integrated intelligent sampling device for efficient and accurate, simultaneous monitoring and complete acquisition of sediments and stratified water sample. Peterson mussel samplers, plunger type column samplers (having an inner diameter of 5 cm, 7.5 cm, 9 cm, etc.) and gravity type column samplers (having an inner diameter of 11 cm) are widely applied only to collection of sediment samples at present. In addition, an underwater sediment sampling robot conceptual model is proposed. Most of these bottom sediment sampling devices are suitable for shallow water sample collection, and there is nowhere to purchase collection devices for sediments and stratified water of deep reservoirs under complicated conditions. This will undoubtedly greatly hinder science researchers from in-depth study and scientific understanding of a deep water environment under complicated conditions.

At present, it is difficult to perform core collection of deep reservoirs and vertical simultaneous water monitoring, mainly in the following aspects: (1) a traditional bottom sediment sampling method is usually to collect bottom sediment by a plunger or adding a counterweight, where a sinking process is often affected by the disturbance of wind waves and water flows, resulting in low collection success rate; (2) it is difficult for a traditional sampling device to observe underwater topography and substrate types in real time, gravity in a sampling process will inevitably cause disturbance of sediment surfaces and destroy an original stratification structure of sediments; (3) when a traditional plunger sampler recovers collected sediment cores, it gradually shifts up along with a sediment column, since the pressure of a water depth changes continuously, near bottom sediment falls, and upper and lower water column are mixed, so that the collected core and part of bottom water bodies are greatly different from actual in-situ redox conditions, and obtained results are often untrue; (4) a traditional method is to separate stratified collections of sediments and overlying water bodies, where without the in-situ real-time monitoring of key physical and chemical parameters of stratified water, it is difficult to match the obtained sediment properties and parameters of the overlying water body effectively; and (5) more importantly, a traditional sampler can only complete the collection of a intact core at one time, and the spatial and temporal heterogeneities of physical and chemical properties of sediments is very large, this sampling method is bound to increase a systematic error between parallel samples, which often leads to difficult effective cross-comparisons between different study results in the same region, thus severely limiting the exchange of academic results and the development of disciplines.

SUMMARY OF THE INVENTION

Objective of the Invention

For the problem in the prior art, the present invention provides a high-dam deep-reservoir stratified water sample and sediment core integrated artificial intelligence sampling device. The sampling device is an intelligent sampling device integrating high-definition underwater topography observation, undisturbed sediment core collection, accurate vertical-stratified water sampling, and real-time field monitoring of key physical and chemical parameters. The device can be flexibly applied to deep and shallow water environments (for example, ultra-deep reservoirs, offshore estuaries, lakes, rivers and other water bodies) under complicated conditions, thereby realizing efficient, accurate and undisturbed collection of a great number of complete sediments and stratified water samples of sequencing batch reactors from lakes, reservoirs, rivers, coasts and other water bodies, and simultaneous completion of real-time in-situ monitoring of key physical and chemical parameters of stratified water samples. The major technical difficulties in the collection of ultra-deep reservoir samples are overcome, and the shortcomings of traditional methods such as low sampling success rate, easy damage of sediments, deviation from in-situ real conditions of samples, poor data matching and large spatial and temporal heterogeneity of sediments are greatly improved.

Technical Solution

To achieve the foregoing objective, a ultra-deep reservoir stratified water sample and intact sediment core integrated intelligent sampling device as described in the present invention includes a sampling device main chamber, an attitude balance sensor, a propeller, a balance base, and a sampler body, wherein the attitude balance sensor and the sampler body are installed inside the sampling device main chamber; the propeller is disposed outside the sampling device main chamber; and the balance base is located at a bottom end of the sampling device main chamber.

The sampler body is mounted inside the sampling device main chamber through a rack, and is sequentially provided with a high frequency vibration sensor, an array type water collector, an array type sediment core collector, a sealed cabin, and an illumination camera system from top to bottom.

According to diverse hydrological conditions, topographical features and substrate types at the bottom of a ultra-deep reservoir water body, an illumination camera system at front and rear ends and in a vector downward direction such as an underwater high-definition camera (underwater image resolution is not lower than 1920×1080 pixels) is provided; in-situ real-time screening of an optimal sampling position is performed to avoid damage to the sampler.

The propeller is a gas propeller, and two to four propellers are disposed outside the sampling device main chamber and evenly distributed outside the sampling device main chamber. By operating a remote control, the horizontal displacement of the propeller in the front-back and left-right directions is triggered, and a gas propeller may also be disposed outside the sampler body to achieve the up-down displacement of the entire sampling device, thereby obtaining an optimal sampling point. Further, a water operator remotely controls the propeller through a control panel, thereby achieving fine posture adjustment of the entire sampling device. Then, the buoyancy is changed by adjusting the attitude balance sensing device and by the pressure adjustment of the sealed cabin, and the sampling device is maintained in a horizontal state, so as to achieve the undisturbed contact of the sampling device to the surface of a sediment to be sampled, thereby effectively preventing the sediment from resuspension under the action of an external force to obtain a complete original sample.

Preferably, the high frequency vibration sensor is a high frequency acoustic vibration sensing device, and the high frequency vibration sensor slowly pushes the array type sediment collector to move down and gradually contacts the surface of the sediment.

The array type water collector is a multi-channel array type water collector, wherein the volume of each single-channel water collector ranges from 500 to 600 ml, and the volume of a collected water sample may also range from 500 to 600 ml. The array type water collector adopts vacuum negative pressure suction to realize the collection of a stratified water sample. The depth of the collected water sample is determined mainly by calibration via a water pressure sensing device provided in the middle of each sampling tube of the array type water collector in the sampler body. According to the water depth and dine seasonal distribution characteristics of a deep reservoir, a single or multiple samples of overlying water bodies within different depth ranges can be selected for simultaneous collection, which effectively satisfies the study of the vertical dine properties of deep water bodies. Moreover, a depth interval of samples can be artificially set according to the vertical variation law of key parameters of deep-reservoir dine water bodies to realize the intelligent and accurate collection of vertical stratified water bodies. The volume of a single-channel collected water sample ranges from 500 to 600 ml, and the volume of each single-channel water collector usually ranges from 500 to 600 ml.

The array type sediment collector is a multi-channel array type sediment collector, the length of a sampling tube of the sediment collector ranging from 50 cm to 200 cm optionally. The length of the sampling tube may be effectively selected according to different purposes of studies, thus meeting different needs of sediment studies in different disciplines.

Further, the array type sediment collector is sealed by a vacuum negative pressure mode, the sampling tube of the array type sediment collector is pushed into an underwater sediment without disturbance by the high frequency vibration sensor, and hard bottom sediment such as gravel and clay is effectively collected by thousands of times of micro vibration per minute, which not only effectively guarantees the sampling depth of the sampling tube for bottom sediment, but also avoids the disturbance and stratification damage caused by a single gravity impact on the bottom sediment, thus improving the success rate and quality of sample collection. The array type sediment collector is sealed by a vacuum negative pressure mode. When a sample is collected and recovered, a sampling failure caused by non-tight sealing through a traditional method will not be repeated, and a sediment in the sampling tube will not fall, thereby effectively guaranteeing the successful collection of a sediment core.

The array type sediment collector focuses on using a high frequency acoustic vibration sensing device to drive a sampling tube of a multi-channel array type sediment collector to collect a complete sediment core sample, and adjusting the high frequency vibration and low-speed rotation of a rotary power head on a high frequency vibration sensor, vibration is formed by repeated oscillation around a balance point, energy accumulates in the sampling tube of the sediment collector, and when an inherent frequency is reached, resonance is caused for release and transmission. The generated energy is efficiently transmitted through a drill pipe, so that the drill pipe is continuously drilled into the sediment. The device effectively avoids the disturbance and destruction of the surface of the sediment by a gravity sampler, thereby obtaining a sediment core sample close to an in-situ condition.

The integrated intelligent sampling device is provided with a water intelligent operating interface, which effectively completes intelligent setting of a sampling process, visual control, and integrated artificial intelligence sample collection, e.g., efficient and accurate integrated in-situ collection of sediment cores. The role of an artificial intelligence technology in the present invention is further improved, and the robustness of the sampling device is enhanced.

Preferably, the integrated intelligent sampling device uses an umbilical cord as a safety rope of the sampling device for secondary protection. When the sampler has a downward vector in water, the safety rope is slowly placed at a constant speed to provide traction energy for the sampler, and the safety rope can also balance and recover the sampling device main chamber.

In addition, a water quality multi-parameter analyzer carried by the array type water collector completes real-time observation of a specific water depth and an entire vertical-profile water body, and transmits monitoring data to a water surface operating system in real time. The array type water collector is provided with a multi-parameter water quality analyzer (YSI, USA), which can simultaneously analyze key physical and chemical parameters such as dissolved oxygen, Redox, temperature, pH, conductivity, salinity and algae density in vertical water, and can simultaneously monitor the properties of stratified water samples to better match the properties of the stratified water samples and sediments with the physical and chemical parameters of the stratified water samples.

Working Principle: At the beginning of sample collection, according to the characteristics of different deep reservoirs and the cline distribution law of water bodies, an operation interface is pre-set on a water surface operation platform to complete the accurate setting and remote control of a distance interval of stratified water samples. An umbilical cord is used as a safety rope of the sampling device for secondary protection. When the entire sampling device has a downward vector in water, the safety rope is slowly placed at a constant speed to provide traction energy for the sampling device. At a pre-set water depth, the attitude of the entire sampling device is balanced by remotely controlling the propeller, and the stratified water samples can be collected by an array type multi-channel water collector. In the profile collection process of the entire stratified water body, a carried water quality multi-parameter analyzer (YSI, USA) is simultaneously used to complete real-time observation of a specific water depth and an entire vertical-profile water body, and to transmit monitoring data to a water surface operating system in real time.

When the sampling device main chamber is about 100 cm away from the surface of a sediment, the propeller is remotely driven by water operation, and then the attitude balance sensing device of the sampling device is used to guide the sampling device to a substantially balanced state. The underwater high-definition camera of the illumination camera system is mainly mounted at front and rear ends of the sampler body and a vector downward position. A water operation panel is used to analyze underwater topography and substrate types, and provides an intuitive high-definition evidence to select an optimal sampling point. When the sampling point is not suitable for the operation, the horizontal displacement of the propeller in the front-back and left-right directions is triggered by operating a remote control, and then the up-down displacement of the sampling device is realized by adjusting the attitude balance sensor, thereby obtaining an optimal sampling point.

After the sampling device base falls stably to the surface of a substrate to be collected, the downward pressure of the sampling device is further increased by adjusting the buoyancy of the sealed cabin, thus providing a stable supporting role for the collection of a sediment core.

The high frequency vibration sensor is remotely controlled to slowly push the sampling tube of the array type sediment collector to move down and gradually contacts the surface of the sediment. A low-speed rotary sampling drill mode is initially used to make the sampling tube enter the sediment without disturbance. After entering the surface sediment for 3 to 5 cm, the sampling tube is pushed into the sediment by a high-speed vibration mode.

After the array type sediment collector completes sediment sampling, the sampling tube is gradually separated from the sediment by adjusting the high frequency vibration sensor, and the sampling device main chamber is maintained in equilibrium by the safety umbilical cord and the gas propeller.

The underwater sampling device main chamber is recovered at a constant speed through the safety umbilical cord, the multi-channel array type water collector and sediment collector are manually removed, and auxiliary components such as an accurate sediment cutting device and an anaerobic glove box are used to obtain in-situ complete stratified water samples and sediment core samples. The entire sampling process is completed so far.

Beneficial Effect: Compared with the prior art, the present invention has the advantages as follows:

The high-dam deep-reservoir stratified water sample and sediment core integrated artificial intelligence sampling device of the present invention has the functions of high-definition underwater topography observation, undisturbed sediment core collection, vertical stratified accurate sampling of water bodies, and simultaneous monitoring of key physical and chemical parameters, and can be flexibly applied to deep and shallow water environments under complicated conditions, thereby realizing efficient, accurate and undisturbed collection of a great number of complete sediments and stratified water samples of sequencing batch reactors from lakes, reservoirs, rivers, coasts and other water bodies, and simultaneous completion of real-time in-situ monitoring of key physical and chemical parameters of stratified water samples. The collection of a high-dam deep-reservoir water sediment and a stratified water sample is effectively provided.

(1) Efficient and undisturbed collection of sediments: During the collection process of underwater sediment cores, the sampling success rate of the device and the degree of disturbance to a sample sediment-water interface are key indicators for evaluating the performance of a bottom sediment sampler. The underwater high-definition cameras with horizontal and downward directions are provided to artificially and intelligently control the displacement of the device, observe the underwater topography and geomorphology in real time, and select an optimal sampling position; after the sampling position is determined, the attitude adjustment of the sampling device is realized by remotely controlling the propeller, the buoyancy is changed to maintain a horizontal state, and the sampling tube is slowly moved to contact a sediment interface to achieve undisturbed sampling, thus greatly improving the success rate and quality of sample collection. Similarly, the sample recovery process is contrary to the above sinking process.

(2) Array type multi-channel collection system: In view of large spatial and temporal differentiation of the physical and chemical properties of water sediments, combined with the deficiency that the traditional sampler can only collect one sample in a single time, the array type multi-channel collection system of the present invention can effectively collect parallel samples of multiple sediments and stratified water bodies at a study point in a single time, and simultaneously achieve a single complete collection of multi-point stratified water samples in a deep water environment.

(3) Accurate collection and simultaneous monitoring of vertical water bodies: For the problem that it is difficult to effectively match sediment properties and parameters of an overlying water body obtained by the traditional method, deep-reservoir vertical stratified accurate water sampling (an error is lower than 0.5 m) is achieved by the negative pressure suction and the water pressure sensing device according to thermocline and oxycline features (usually within a water depth range of 30 to 50 m) in different water periods of deep reservoirs, and the accurate collection of a dine interval water body is focused. In addition, a multi-parameter water quality analyzer (YSI, USA) is provided to simultaneously determine key physical and chemical parameters such as dissolved oxygen, Redox, temperature, pH, conductivity, salinity and algae density in vertical water.

DETAILED DESCRIPTION OF THE INVENTION

The present invention will be further described below in conjunction with the drawings and embodiments.

Embodiment

Figure 1:
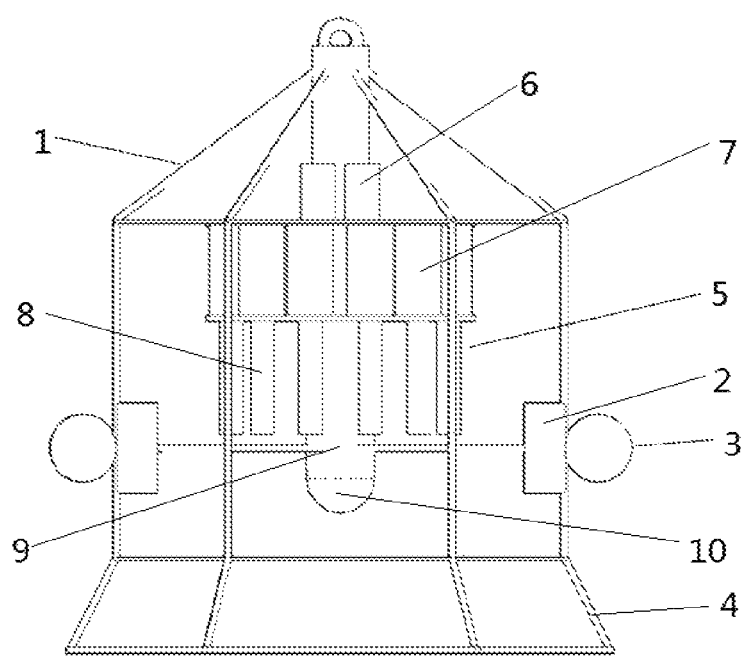
FIG. 1 is a structural schematic diagram of a sampling device main chamber according to an embodiment of the present invention.
Figure 2:
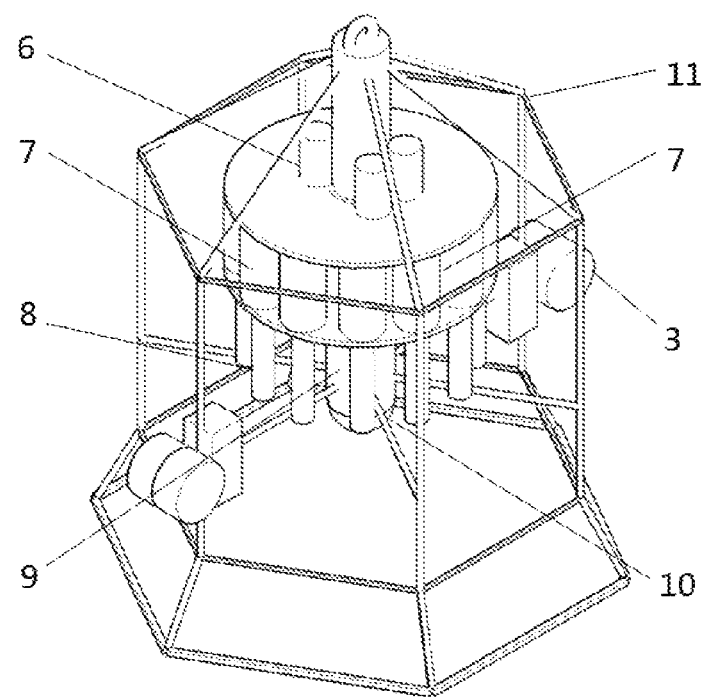
FIG. 2 is a structural schematic diagram of a sampler body according to an embodiment of the present invention.

As shown in FIGS. 1-2, a high-dam deep-reservoir stratified water sample and sediment core integrated artificial intelligence sampling device includes a sampling device main chamber 1, an attitude balance sensor 2, a propeller 3, a balance base 4, and a sampler body 5. The attitude balance sensor 2 and the sampler body 5 are disposed inside the sampling device main chamber 1; the propeller 3 is disposed outside the sampling device main chamber 1; and the balance base 4 is located at a bottom end of the sampling device main chamber 1. The sampler body 5 is mounted inside the sampling device main chamber 1 through a rack 11, both sides of the sampler body 5 are provided with the attitude balance sensor 2, and the sampler body is sequentially provided with a high frequency vibration sensor 6, an array type water collector 7, an array type sediment collector 8, a sealed cabin 9, and an illumination camera system 10 from top to bottom. The propeller 3 is a gas propeller, and two to four propellers are disposed outside the sampling device main chamber 1 and evenly distributed outside the sampling device main chamber 1. Moreover, a gas propeller may also be disposed outside the sampler body 5 to achieve the up-down displacement of the entire sampling device, thereby obtaining an optimal sampling point.

The array type water collector 7 is a multi-channel array type water collector, wherein the volume of each single-channel water collector ranges from 500 to 600 ml. The array type water collector 7 adopts vacuum negative pressure suction to complete. The depth of the collected stratified water sample is determined mainly by a water pressure sensing device. A motor sealed main chamber is provided in the middle of the array type water collector 7. The high frequency vibrator 6 is electrically propelled to provide energy for a sampling action of the array type sediment collector 8. The array type water collector 7 is further provided with a water quality multi-parameter analyzer (YSI, USA), which completes real-time observation of a specific water depth and an entire vertical-profile water body, and transmits monitoring data to a water surface operating system in real time.

The array type sediment collector 8 is a multi-channel array type sediment collector, and the length of a sampling tube of the sediment collector ranges from 50 cm to 200 cm. The array type sediment collector 8 is sealed by a vacuum negative pressure mode, the sampling tube of the array type sediment collector 8 is pushed into an underwater sediment without disturbance by the high frequency vibration sensor 6, and hard bottom sediment is effectively collected by thousands of times of micro vibration per minute, wherein the high frequency vibration sensor 6 is a high frequency acoustic vibration sensing device.

The high-dam deep-reservoir stratified water sample and sediment core integrated intelligent sampling device is further provided with a water intelligent operating interface, which effectively completes intelligent setting of a sampling process, visual control, and integrated intelligent sample collection. The present sampling device uses an umbilical cord as a safety rope of the sampling device for secondary protection.

At the beginning of sample collection, according to the characteristics of different deep reservoirs and the dine distribution law of water bodies, an operation interface is pre-set on a water surface operation platform to complete the accurate setting and remote control of a distance interval of stratified water samples. An umbilical cord is used as a safety rope of the sampling device for secondary protection. When the entire sampling device has a downward vector in water, the safety rope is slowly placed at a constant speed to provide traction energy for the entire sampling device. At a pre-set water depth, the attitude of the sampling device main chamber 1 is balanced by remotely controlling the propeller 3 and the attitude balance sensor 2, and the stratified water samples can be collected by the multi-channel array type water collector 7. In the profile collection process of the entire stratified water body, a carried water quality multi-parameter analyzer (YSI, USA) is simultaneously used to complete real-time observation of a specific water depth and an entire vertical-profile water body, and to transmit monitoring data to a water surface operating system in real time.

When the sampling device main chamber 1 is about 100 cm away from the surface of a sediment, the propeller 3 is remotely driven by water operation, and then the attitude balance sensing device of the sampling device namely the attitude balance sensor 2 is used to guide the sampling device to a substantially balanced state. An underwater high-definition camera of the illumination camera system 10 is mainly mounted at front and rear ends of the sampler body and a vector downward position. A water operation panel is used to analyze underwater topography and substrate types, and provides an intuitive high-definition evidence to select an optimal sampling point. When the sampling point is not suitable for the operation, the propeller 3 is triggered by operating a remote control to adjust the position of the entire sampling device, and then the fine attitude adjustment of the entire sampling device is realized by adjusting the attitude balance sensor 2 on the sampling device, thereby obtaining an optimal sampling point.

After the sampling device base falls stably to the surface of a substrate to be collected, the downward pressure of the sampling device is further increased by adjusting the buoyancy of the sealed cabin, thus providing a stable supporting role for the collection of a sediment core.

The high frequency vibration sensor is remotely controlled to slowly push the sampling tube of the array type sediment collector to move down and gradually contacts the surface of the sediment. A low-speed rotary sampling drill mode is initially used to make the sampling tube enter the sediment without disturbance. After entering the surface sediment for 3 to 5 cm, the sampling tube is pushed into the sediment by a high-speed vibration mode.

After the array type sediment collector completes sediment sampling, the sampling tube is gradually separated from the sediment by adjusting the high frequency vibration sensor, and the sampling device main chamber is maintained in equilibrium by the safety umbilical cord, the propeller 3 and the attitude balance sensing device 2.

The entire underwater sampling device is recovered at a constant speed through the safety umbilical cord, the multi-channel array type water collector and sediment collector are manually removed, and auxiliary components such as an accurate sediment cutting device and an anaerobic glove box are used to obtain in-situ complete stratified water samples and sediment core samples. The entire sampling process is completed so far.

What is claimed is:

1. A high-dam deep-reservoir stratified water sample and sediment core integrated artificial intelligence sampling method, wherein a sampling device adopted by the sampling method comprises a sampling device main chamber (1), an attitude balance sensor (2), a propeller (3), a balance base (4), and a sampler body (5); the attitude balance sensor (2) and the sampler body (5) are disposed inside the sampling device main chamber (1); the propeller (3) is disposed outside the sampling device main chamber (1); the balance base (4) is located at a bottom end of the sampling device main chamber (1); and the sampler body (5) is sequentially provided with a high frequency vibration sensor (6), an array type water collector (7), an array type mud collector (8), a sealed cabin (9), and an illumination camera system (10) from top to bottom; and the array type water collector (7) is a disc-shaped multi-channel array type water collector, the array type water collector (7) sucks under vacuum pressure, and each sampling tube of the water collector is provided with a water pressure sensing device;

the array type mud collector (8) is a disc-shaped multi-channel array type mud collector, the array type mud collector (8) is sealed by a vacuum negative pressure mode, the sampling tube of the array type mud collector (8) is pushed into an underwater sediment by the high frequency vibration sensor (6), the disc-shaped multi-channel array type mud collector is independently positioned below the disc-shaped multi-channel array type water collector, and the disc area formed by the disc-shaped multi-channel array type mud collector is smaller than that formed by the disc-shaped multi-channel array type water collector;

the sampling device is provided with a water intelligent operating interface; the sampling device uses an umbilical cord as a safety rope of the sampling device; and a water quality multi-parameter analyzer is carried by the array type water collector (7);

the sampling method comprises the following steps:

(1) at the beginning of sample collection, according to the characteristics of different deep reservoirs and the dine distribution law of water bodies, pre-setting on a water intelligent operating interface to complete accurate setting and remote control of a distance interval of stratified water samples; using the umbilical cord as the safety rope of the sampling device for secondary protection; when the entire sampling device has a downward vector in water, placing the safety rope to provide traction energy for the entire sampling device; at a pre-set water depth, balancing the attitude of the sampling device main chamber (1) by remotely controlling the propeller (3) and the attitude balance sensor (2), and then collecting the stratified water samples by the multi-channel array type water sampler (7); and in the profile collection process of the entire stratified water body, using a carried water quality multi-parameter analyzer simultaneously to complete real-time observation of a specific water depth and an entire vertical-profile water body, and transmitting monitoring data to a system of the water intelligent operating interface in real time;

(2) when the sampling device main chamber (1) is 100 cm away from the surface of a sediment, remotely driving the propeller (3) by water operation, and then using the attitude balance sensor (2) to guide the sampling device to a balanced state; locating an underwater high-definition camera of the illumination camera system (10) at front and rear ends of the sampler body (5) and a vector downward position; using a water intelligent operating interface to analyze underwater topography and substrate types, and selecting an optimal sampling point; and when the sampling point is not suitable for the operation, triggering the propeller (3) by operating a remote control to adjust the position of the entire sampling device, and then realizing the fine attitude adjustment of the entire sampling device by adjusting the attitude balance sensor (2) on the sampling device, thereby obtaining an optimal sampling point;

(3) after the sampling device balance base (4) falls stably to the surface of a substrate to be collected, further increasing the downward pressure of the sampling device by adjusting the buoyancy of the sealed cabin (9), thus providing a stable supporting role for the collection of a sediment core;

(4) remotely controlling the high frequency vibration sensor (6) to slowly push the sampling tube of the array type mud collector (8) to move down and gradually contact the surface of the sediment; initially using a low-speed rotary sampling drill mode to make the sampling tube enter the sediment without disturbance; and after the sampling tube enters the surface sediment for 3 to 5 cm, pushing the sampling tube into the sediment by a high-speed vibration mode;

(5) after the array type mud collector (8) completes sediment sampling, gradually separating the sampling tube from the sediment by adjusting the high frequency vibration sensor (6), and maintaining the sampling device main chamber in equilibrium by the safety umbilical cord, the propeller (3) and the attitude balance sensing device (2); and (6) recovering the entire underwater sampling device through the safety umbilical cord, removing the array type water collector (7) and the array type mud collector (8), and using auxiliary components such as an accurate sediment cutting device and an anaerobic glove box to obtain in-situ complete stratified water samples and sediment core samples; and completing the entire sampling process so far.

2. The high-dam deep-reservoir stratified water sample and sediment core integrated artificial intelligence sampling device according to claim 1, wherein the propeller (3) is a gas propeller.

3. The high-dam deep-reservoir stratified water sample and sediment core integrated artificial intelligence sampling device according to claim 1, wherein two to four propellers (3) are disposed outside the sampling device main chamber (1).

4. The high-dam deep-reservoir stratified water sample and sediment core integrated artificial intelligence sampling device according to claim 1, wherein the high frequency vibration sensor (6) is a high frequency acoustic vibration sensing device, the sampling tube of the array type mud collector (8) is pushed into an underwater sediment by the high frequency vibration sensor (6), and hard bottom mud is effectively collected by thousands of times of micro vibration per minute.

5. The high-dam deep-reservoir stratified water sample and sediment core integrated artificial intelligence sampling device according to claim 1, wherein the volume of each single-channel water collector of the array type water collector (7) ranges from 500 to 600 ml.

6. The high-dam deep-reservoir stratified water sample and sediment core integrated artificial intelligence sampling device according to claim 1, wherein the length of each sampling tube of the array type mud collector (8) ranges from 50 cm to 200 cm.

* * * * *